United States Patent
Hong et al.

(10) Patent No.: US 12,428,371 B2
(45) Date of Patent: Sep. 30, 2025

(54) PREPARATION METHOD FOR METFORMIN HYDROCHLORIDE

(71) Applicant: ASYMCHEM LIFE SCIENCE (TIANJIN) CO., LTD, Tianjin (CN)

(72) Inventors: Hao Hong, Morrisville, NC (US); Jiangping Lu, Tianjin (CN); Jian Tao, Tianjin (CN); Yan Zhang, Tianjin (CN); Fan Wang, Tianjin (CN); Gonzalez Miguel, Morrisville, NC (US)

(73) Assignee: ASYMCHEM LIFE SCIENCE (TIANJIN) CO., LTD, Tianjin (CN)

( * ) Notice: Subject to any disclaimer, the term of this patent is extended or adjusted under 35 U.S.C. 154(b) by 789 days.

(21) Appl. No.: 17/629,840

(22) PCT Filed: Jul. 25, 2019

(86) PCT No.: PCT/CN2019/097762
§ 371 (c)(1),
(2) Date: Jan. 25, 2022

(87) PCT Pub. No.: WO2021/012274
PCT Pub. Date: Jan. 28, 2021

(65) Prior Publication Data
US 2022/0251034 A1   Aug. 11, 2022

(51) Int. Cl.
*C07C 277/06* (2006.01)

(52) U.S. Cl.
CPC ........ *C07C 277/06* (2013.01); *C07B 2200/13* (2013.01)

(58) Field of Classification Search
None
See application file for complete search history.

(56) References Cited

FOREIGN PATENT DOCUMENTS

| CN | 104788345 A | 7/2015 |
|---|---|---|
| CN | 105968032 A | 9/2016 |
| CN | 108178738 A | 6/2018 |
| CN | 109535279 A | 3/2019 |
| WO | 2014041566 A2 | 3/2014 |

OTHER PUBLICATIONS

Anvar Shalmashi, "New Route to Metformin Hydrochloride (N, N-dimethylimidodicarbonimidic diamide hydrochloride) Synthesis", Iranian Research Organization for Science and Technology, Aug. 27, 2007.
International Search Report for corresponding application PCT/CN2019/097762 filed Jul. 25, 2019; Mail date Apr. 15, 2020.
Shaminder Singh, "Design, Synthesis, biological evaluation and toxicity studies of N, N-disubstituted biguanides as quorum sensing inhibitors", Medicinal Chemistry Research, Oct. 7, 2014.
Written Opinion of the International Searching Authority for corresponding application PCT/CN2019/097762 filed Jul. 25, 2019; Mail date Apr. 15, 2020.

*Primary Examiner* — Renee Claytor
*Assistant Examiner* — Jennifer C Sawyer
(74) *Attorney, Agent, or Firm* — CANTOR COLBURN LLP

(57) ABSTRACT

The present disclosure provides a preparation method for metformin hydrochloride. The preparation method includes: microwave heating raw materials containing dicyandiamide and dimethylamine hydrochloride, and reacting the two at 100° C. to 160° C. to obtain a product system containing metformin hydrochloride. Microwave heating is adopted to heat the dicyandiamide and the dimethylamine hydrochloride. Compared with a conventional heating mode that requires heat to be gradually transferred from the outside to the inside, microwave heating can directly heat each part inside the reactant, which can make the internal temperature of the reactant more uniform, thereby reducing the generation of impurities.

19 Claims, No Drawings

PREPARATION METHOD FOR METFORMIN HYDROCHLORIDE

TECHNICAL FIELD

The present disclosure relates to the field of synthesis of metformin hydrochloride, in particular to a preparation method for metformin hydrochloride.

BACKGROUND

Metformin is mainly used for type 2 diabetes, which is ineffective in pure diet control and physical exercise treatment, especially obese type 2 diabetes. It is combined use with insulin can reduce the amount of insulin and prevent hypoglycemia. Moreover, it has a synergistic effect in combination with sulfonylurea hypoglycemic agents. Metformin hydrochloride has become the cornerstone of diabetes treatment, and has also become a reference for the development of new diabetes drugs. The evaluation of new oral hypoglycemic agents is to confirm that its efficacy is "equal or better than metformin". In 2001, the sales of glucophage reached a record of 2.7 billion dollars, with an increase of 42%, and the prescription dosage exceeded one-third of the total prescription dosage of oral hypoglycemic agents. It became the first choice among oral hypoglycemic agents at that time.

In the prior art, high-purity metformin hydrochloride production methods include a solvent method, a melting method and a solvent high-pressure synthesis method. Among them, Chinese patent publication No. CN104788345A discloses a method for synthesizing metformin hydrochloride by a solvent method using N-methylpyrrolidone as a solvent and using dicyandiamide and dimethylamine hydrochloride as solutes. Specifically, the above materials are added into a synthesis kettle for reaction, and the metformin hydrochloride is prepared through the steps of stirring, cooling, spin-drying, washing, crystallizing and drying. Chinese patent application publication No. CN108178738A discloses a method and system for synthesizing metformin hydrochloride by a melting method, wherein a spiral device is used to synthesize the metformin hydrochloride, its synthesis system comprises a reaction device, and a feeding port and a reaction material discharging port are formed in the reaction device for synthesizing the metformin hydrochloride with the melting method; a spiral discharging part is arranged in the reaction device to discharge the metformin hydrochloride from the reaction material discharging port. Reaction raw materials are added from the feeding port, and the spiral discharging part can discharge reaction products from the reaction material discharging port through spiral extrusion, so that the problem that stirring cannot be performed due to high stirring resistance of solid materials is solved. Chinese patent publication No. CN105968032B discloses a high-pressure synthesis method using water as a solvent. In a high pressure enclosed environment, dimethylamine, dicyandiamide, a hydrochloric acid solution, and a catalyst organic acid are added, and a heating reaction is carried out in order to obtain metformin hydrochloride.

The traditional solvent method has a long reaction time. For commercial products, due to heating in the reaction kettle, the inside and the outside are heated unevenly, and the reaction time is too long, resulting in generating more impurities in the product; meanwhile, an organic solvent is introduced in the reaction, such as N-methylpyrrolidone, toluene, etc., which are all slightly toxic to the human body. The solid melting method adopts a spiral extrusion device, which has limited production capacity in industrialization and has high requirements for mechanical materials, so that heavy metal impurities will be introduced, and the airtightness cannot be guaranteed; during the reaction, the solid two phases will release heat instantly, and overheating will cause product deterioration, and from the point of view of mechanical equipment, it is difficult to extract heat from the spiral reactor, and precise temperature control cannot be achieved. The disadvantages of the water-solvent high-pressure method lie in that the process safety factor is low, and that it is not suitable for continuous industrial production, meanwhile, a large amount of waste acid will be generated, which increases the cost of subsequent wastewater treatment and does not conform to the green chemical synthesis process.

It can be seen that in the prior art, the production of the metformin hydrochloride has the disadvantages of low purity, low yield, long cycle, high cost, potential safety hazards in production, environmental pollution, etc. In the production of the metformin hydrochloride, the most critical thing is the addition reaction of the dicyandiamide and the dimethylamine hydrochloride. In order to improve the efficiency of the addition reaction, the research and application on the preparation of raw material dimethylamine hydrochloride, the drying of finished products, etc., at home and abroad have become increasingly mature. But its research value is not as good as the addition reaction of the dicyandiamide and the dimethylamine hydrochloride. In recent years, the metformin hydrochloride has a breakthrough in the preparation of drugs for the treatment of Parkinson's disease, and more stringent requirements have been put forward for its purity and impurity content; in addition, the metformin hydrochloride has also made new developments in the synthesis of other drugs, and the preparation of products with high content of metformin hydrochloride and low content of impurities such as dicyandiamide, dimethylamine, tetracyanamide is the focus of attention and research in the same industry at home and abroad.

SUMMARY

The main purpose of the present disclosure is to provide a preparation method for metformin hydrochloride to solve the problem of low purity of metformin hydrochloride obtained by the preparation method in the prior art.

In order to achieve the purpose, according to one aspect of the present disclosure, a preparation method for metformin hydrochloride is provided. The preparation method comprises: microwave heating raw materials containing dicyandiamide and dimethylamine hydrochloride, and reacting the two at 100° C. to 160° C. to obtain a product system containing metformin hydrochloride.

Further, the preparation method comprises: mixing the dicyandiamide and the dimethylamine hydrochloride to form a first mixed system; microwave heating and melting the first mixed system to obtain a system to be reacted; and controlling the temperature of the system to be reacted at 100° C. to 160° C. for reaction, so as to obtain the product system.

Further, the preparation method comprises: mixing a solvent, the dicyandiamide and the dimethylamine hydrochloride to form a second mixed system; microwave heating the second mixed system to dissolve the dicyandiamide and the dimethylamine hydrochloride into the solvent to form a system to be reacted; and controlling the temperature of the system to be reacted at 100° C. to 160° C. for reaction, so as to obtain the product system.

Further, in the preparation method, a metformin hydrochloride crystal nucleus is added to the solvent before microwave heating, or a metformin hydrochloride crystal nucleus is added when the temperature of the system to be reacted increases to 100° C. to 160° C., and the weight ratio of the metformin hydrochloride crystal nucleus to the dicyandiamide is preferably 0.0015-0.0045:100.

Further, the solvent is selected from any one of a group composed of ethanol, cyclohexanol, mesitylene, diphenyl and N-methylpyrrolidone, the molar ratio of the dicyandiamide to the solvent is preferably 1:1 to 1:5, and more preferably 1:1 to 1:3.

Further, the molar ratio of the dicyandiamide to the dimethylamine hydrochloride is 1:1 to 1:2.

Further, the temperature of the system to be reacted is controlled between 100° C. to 160° C., preferably 155° C. to 160° C. by cooperation of intermittent microwave heating and external condensation.

Further, the process of forming the above system to be reacted and the reaction process of the system to be reacted are carried out under stirring, the stirring speed in the process of forming the system to be reacted is preferably 300 rpm to 400 rpm, the stirring speed in the reaction process of the system to be reacted is preferably 100 rpm to 400 rpm, and the stirring speed in the crystallization phase in the reaction process of the system to be reacted is more preferably 100 rpm to 300 rpm.

Further, the power of the above microwave heating is 100 W to 1000 W.

Further, the reaction pressure in the reaction process of the above system to be reacted is controlled between 95 KPa to 105 KPa.

Further, after crystals are precipitated in the above system to be reacted, the temperature is kept for 30 minutes to 60 minutes.

Further, the above preparation method further comprises a process of purifying the metformin hydrochloride from the product system, the process of purifying the metformin hydrochloride preferably comprises: cooling the temperature of the product system to 85° C. to 95° C., and then mixing the product system with ethanol to form a solid-liquid mixed system; subjecting the solid-liquid mixed system to solid-liquid separation to obtain a solid product and a liquid isolate; and washing the solid product with ethanol, carrying out solid-liquid separation and drying, so as to obtain purified metformin hydrochloride.

By applying the technical solution of the present disclosure, microwave heating is adopted to heat the dicyandiamide and the dimethylamine hydrochloride. Compared with a conventional heating mode that requires heat to be gradually transferred from the outside to the inside, microwave heating can directly heat each part inside the reactant, which can make the internal temperature of the reactant more uniform, thereby reducing the generation of impurities. Specifically, the microwave can quickly heat the two reactants so that the reactants reach a molten state or a fast-moving state, and the vibration between reactant atoms can be excited faster by the microwave, so that the reaction energy level is exceeded to quickly produce the product. Meanwhile, due to the relatively high controllable degree of the microwave heating, the microwave heating is stopped when the temperature reaches the required temperature for the reaction. Once the heat source is withdrawn, the exothermic heat of the reaction itself can be utilized to maintain the preset reaction temperature and continue the reaction. When heating is needed, the microwave can be turned on again, which can further reduce the generation of impurities. Moreover, due to the relatively high efficiency of the microwave heating, the use of microwave heating to synthesize the metformin hydrochloride can greatly shorten the reaction time. Therefore, the use of microwave heating to synthesize the metformin hydrochloride can improve the purity of the metformin hydrochloride, and is suitable for a melting method and a solvent method, thereby greatly reducing the difficulty of production, simplifying the process flow, and providing more feasible solutions for industrialization.

DETAILED DESCRIPTION OF THE EMBODIMENTS

It should be illustrated that the embodiments in the present application and the features in the embodiments can be combined with each other in the case of no conflict. The present disclosure will be described in detail below in combination with the embodiments.

As analyzed in the background of the present application, the metformin hydrochloride obtained by the methods for synthesizing metformin hydrochloride in the prior art has a high content of impurities such as dicyandiamide and dimethylamine, resulting in a low purity of metformin hydrochloride. In order to solve this problem, the present application provides a preparation method for metformin hydrochloride. In an exemplary implementation of the present application, the preparation method comprises: microwave heating raw materials containing dicyandiamide and dimethylamine hydrochloride, and reacting the two at 100° C. to 160° C. to obtain a product system containing metformin hydrochloride as a main product.

The present application adopts microwave heating to heat the dicyandiamide and the dimethylamine hydrochloride. Compared with a conventional heating mode that requires heat to be gradually transferred from the outside to the inside, microwave heating can directly heat each part inside the reactant, which can make the internal temperature of the reactant more uniform, thereby reducing the generation of impurities. Specifically, the microwave can quickly heat the two reactants so that the reactants reach a molten state or a fast-moving state, and the vibration between reactant atoms can be excited faster by the microwave, so that the reaction energy level is exceeded to quickly produce the product. Meanwhile, due to the relatively high controllable degree of the microwave heating, the microwave heating is stopped when the temperature reaches the required temperature for the reaction. Once the heat source is withdrawn, the exothermic heat of the reaction itself can be utilized to maintain the preset reaction temperature and continue the reaction. When heating is needed, the microwave can be turned on again, which can further reduce the generation of impurities. Moreover, due to the relatively high efficiency of the microwave heating, the use of microwave heating to synthesize the metformin hydrochloride can greatly shorten the reaction time. Therefore, the use of microwave heating to synthesize the metformin hydrochloride can improve the purity of the metformin hydrochloride, and is suitable for a melting method and a solvent method, thereby greatly reducing the difficulty of production, simplifying the process flow, and providing more feasible solutions for industrialization.

As mentioned above, the preparation method of the present application can be applied to the melting method or the solvent method to synthesize the metformin hydrochloride. In one embodiment, the above preparation method comprises: mixing the dicyandiamide and the dimethylamine hydrochloride to form a first mixed system; microwave heating and melting the first mixed system to obtain a system to be reacted; and controlling the temperature of the system to be reacted at 100° C. to 160° C. for reaction, so as to obtain the product system. Due to the high efficiency of microwave heating and the uniformity of heating, the dicyandiamide and the dimethylamine hydrochloride can be quickly molten and quickly react, thereby reducing the occurrence of side reactions and improving product purity.

In another embodiment, the above preparation method comprises: mixing a solvent, the dicyandiamide and the dimethylamine hydrochloride to form a second mixed system; microwave heating the second mixed system to dissolve the dicyandiamide and the dimethylamine hydrochloride into the solvent to form a system to be reacted; and controlling the temperature of the system to be reacted at 100° C. to 160° C. for reaction, so as to obtain the product system. The above preparation method is a solvent method. The dicyandiamide and the dimethylamine hydrochloride are dissolved into the solvent to form the second mixed system, and then microwave heating is carried out, which can make the dispersed dicyandiamide and dimethylamine hydrochloride be quickly heated to the reaction temperature and vibrate to participate in the reaction; meanwhile, the mass transfer of each material in the solvent is more efficient, and the purity of its product is improved more obviously.

In the preparation method of the present application, as the reaction progresses, the above system to be reacted will precipitate crystals after a period of time, preferably, after the crystals are precipitated in the system to be reacted, the temperature is kept for 30 minutes to 60 minutes, which can make the reaction complete.

In order to further accelerate crystal precipitation and product generation, preferably, in the above preparation method, a metformin hydrochloride crystal nucleus is added to the solvent before microwave heating, or a metformin hydrochloride crystal nucleus is added when the temperature of the system to be reacted increases to 100° C. to 160° C., and the weight ratio of the metformin hydrochloride crystal nucleus to the dicyandiamide is preferably 0.0015-0.0045: 100.

The solvent adopted in the solvent method of the present application may be selected from the solvent adopted in the conventional solvent method, preferably, the above solvent is selected from any one of a group composed of ethanol, cyclohexanol, mesitylene, diphenyl and N-methylpyrrolidone. Due to the advantages of microwave heating, the selection of the solvent can be made less stringent. When the above solvents are applied in the present application, relatively high purity metformin hydrochloride can be obtained. In addition, in order to further improve the dispersibility of the materials, the molar ratio of the dicyandiamide to the solvent is preferably 1:1 to 1:5; in order to increase the product yield, it is more preferably 1:1 to 1:3.

The dosages of the dicyandiamide and the dimethylamine hydrochloride in the present application may refer to the prior art. In order to save costs, the molar ratio of the above dicyandiamide to the dimethylamine hydrochloride is preferably 1:1 to 1:2, further preferably 1:1 to 1:1.2.

In order to further accurately control the temperature of the reaction process, preferably, the temperature of the system to be reacted is controlled between 100° C. to 160° C., preferably 155° C. to 160° C. by cooperation of intermittent microwave heating and external condensation. Specifically, the microwave is utilized to heat the system to be reacted to the required temperature for the reaction. When the temperature is exceeded, microwave heating is stopped. Due to the reaction releases heat, if the temperature continues to increase, external condensation equipment is utilized to cool the materials so that its temperature is controlled within the temperature range required for the reaction. Through this process, the actual reaction temperature is controlled more stringently, thereby further reducing the generation of impurities. The above external condensation may be implemented by adopting a water cooling device, an air cooling device or a vacuumizing cooling device, and the specific implementation mode can refer to the prior art, which will not be repeated here.

In order to further improve the uniformity of material contact, preferably, the process of forming the system to be reacted and the reaction process of the system to be reacted are carried out under stirring, the stirring speed in the process of forming the system to be reacted is preferably 300 rpm to 400 rpm, the stirring speed in the reaction process of the system to be reacted is preferably 100 rpm to 400 rpm, and the stirring speed in the crystallization phase in the reaction process of the system to be reacted is more preferably 100 rpm to 300 rpm, preferably 150 rpm to 250 rpm. Reducing the stirring speed in the crystallization phase is beneficial to the growth of crystal grains. However, if the stirring speed is too low, the purity of the product will be reduced. In the present application, commercial microwave heating equipment in the prior art is adopted to implement the above heating. In order to better adapt to the reaction rate of the dicyandiamide and the dimethylamine hydrochloride, the power of the above microwave heating is preferably 100 W to 1000 W, more preferably 500 W. When a relatively high power microwave is adopted for heating, the control over tuning on and off of microwave heating needs to be more precise, and a temperature sensor may be designed to be electrically connected with a microwave heater to realize automatic control.

In addition, in order to reduce the occurrence of side reactions, the reaction pressure in the reaction process of the system to be reacted is preferably controlled between 95 KPa to 105 KPa, specifically, an open reaction vessel may be used in the reaction process to make the reaction pressure about the normal pressure. In the present application, after the product system obtained by the above process is purified by a conventional purification method in the prior art, the purity of the obtained metformin hydrochloride can generally reach more than 99%. In order to control the product purity more stably, preferably, the above preparation method further comprises a process of purifying the metformin hydrochloride from the product system, the process of purifying the metformin hydrochloride preferably comprises: cooling the temperature of the product system to 85° C. to 95° C., and then mixing the product system with ethanol to form a solid-liquid mixed system; subjecting the solid-liquid mixed system to solid-liquid separation to obtain a solid product and a liquid isolate; and washing the solid product with ethanol, carrying out solid-liquid separation and drying, so as to obtain purified metformin hydrochloride. The above solid-liquid separation may be filtration or centrifugation.

The beneficial effects of the present application will be further illustrated below in combination with the embodiments and comparative embodiments.

Embodiment 1

Dicyandiamide (120 g), dimethylamine hydrochloride (139.7 g), and cyclohexanol (360 mL) at a molar ratio of 1:1:3 were added into a glass reaction kettle to be mixed to form a mixed system. The mixed system was dissolved under the conditions of microwave heating and stirring at 400 rpm to form a system to be reacted. Microwave heating was utilized to increase the temperature of the system to be reacted to 155° C. 5 mg of metformin hydrochloride was added as a crystal nucleus at 155° C. After the system to be reacted was controlled to be stirred for about 18 minutes at 400 rpm at 155° C. to 160° C., a large amount of solids were generated, then a stirring speed was reduced to 200 rpm, the temperature was controlled between 155° C. to 160° C. by cooperation of microwave heating and condensation of external condensation equipment, and this temperature was totally controlled for 60 minutes, so as to obtain a product system. Then the temperature of the product system was cooled to 90° C., 3 v (360 mL) ethanol was added into it for stirring and washing, filtering was carried out to obtain a filter cake, this filter cake was stirred and washed with 2 v (240 mL) ethanol, filtered and dried, and through nuclear magnetism verification, an obtained product was metformin hydrochloride. The power of the above microwave heating was 500 W, and the reaction kettle was set to be open in the reaction process, so as to control the pressure in the reaction process to be about the normal pressure.

Embodiment 2

Dicyandiamide (120 g), and dimethylamine hydrochloride (139.7 g) at a molar ratio of 1:1 were added into a ceramic reaction kettle to be mixed to form a mixed system. This mixed system was molten under the conditions of microwave heating and stirring at 400 rpm to form a system to be reacted. After melting, heating continues, and when the temperature increased to 155° C., 2 mg of metformin hydrochloride was added as a crystal nucleus. After the system to be reacted was controlled to be stirred for about 15 min at 400 rpm at 155° C. to 160° C., a large amount of solids were generated, then a stirring speed was reduced to 200 rpm, the temperature was controlled between 155° C. to 160° C. by cooperation of microwave heating and condensation of external condensation equipment, and this temperature was totally controlled for 30 minutes, so as to obtain a product system. Then the temperature of the product system was cooled to 90° C., and 3 v (360 mL) ethanol was added into it for stirring and washing. Due to solids in the product system were too hard, strong stirring was required to disperse them. Then filtering was carried out to obtain a filter cake, this filter cake was stirred and washed with 2 v (240 mL) ethanol, filtered and dried, and through nuclear magnetism verification, an obtained product was metformin hydrochloride. The power of the above microwave heating was 500 W, and the reaction kettle was set to be open in the reaction process, so as to control the pressure in the reaction process to be about the normal pressure.

Embodiment 3

Dicyandiamide (1 g), dimethylamine hydrochloride (1.16 g), and ethanol (5 mL) at a molar ratio of 1:1.2:5 were added into a PTFE reaction kettle to be mixed, and then 3 mg of metformin hydrochloride was added as a crystal nucleus to form a mixed system. The mixed system was dissolved under the conditions of microwave heating and stirring at 400 rpm to form a system to be reacted. The temperature continued to increase to 155° C. to 160° C. The pressure of the PTFE reaction kettle was controlled between 1.0 to 1.5 Mpa. After a stirring reaction for about 18 minutes at 400 rpm at 155° C. to 160° C., a large amount of solids were generated, then a stirring speed was reduced to 250 rpm, the temperature was controlled between 155° C. to 160° C. by cooperation of microwave heating and condensation of external condensation equipment, and this temperature was totally controlled for 60 minutes, so as to obtain a product system. Then the temperature of the product system was cooled to 90° C., stirring and cooling were carried out, and filtering was carried out to obtain a filter cake. The filter cake was stirred and washed with 2 v (2 mL) ethanol, filtered and dried, and through nuclear magnetism verification, an obtained product was metformin hydrochloride. The power of the above microwave heating was 500 W.

Embodiment 4

Dicyandiamide (1 g), dimethylamine hydrochloride (1.16 g), and isopropyl (5 mL) at a molar ratio of 1:1:5 were added into a glass reaction kettle to be mixed, and then 3 mg of metformin hydrochloride was added as a crystal nucleus to form a mixed system. The mixed system was dissolved under the conditions of microwave heating and stirring at 400 rpm to form a system to be reacted. The temperature continued to increase to 155° C. to 160° C. The pressure of the glass reaction kettle was controlled between 1.0 to 1.5 Mpa. After a stirring reaction for about 18 minutes at 400 rpm at 155° C. to 160° C., a large amount of solids were generated, then a stirring speed was reduced to 200 rpm, the temperature was controlled between 155° C. to 160° C. by cooperation of microwave heating and condensation of external condensation equipment, and this temperature was totally controlled for 60 minutes, so as to obtain a product system. Then the temperature of the product system was cooled to 90° C., stirring and cooling were carried out, and filtering was carried out to obtain a filter cake. The filter cake was stirred and washed with 2 v (2 mL) ethanol, filtered and dried, and through nuclear magnetism verification, an obtained product was metformin hydrochloride. The power of the above microwave heating was 500 W.

Embodiment 5

Dicyandiamide (120 g), dimethylamine hydrochloride (139.7 g), and mesitylene (120 mL) at a molar ratio of 1:1:1 were added into a glass reaction kettle to be mixed to form a mixed system. The mixed system was dissolved under the conditions of microwave heating and stirring at 400 rpm to form a system to be reacted. Microwave heating was utilized to increase the temperature of the system to be reacted to 155° C. 5 mg of metformin hydrochloride was added as a crystal nucleus at 155° C. After the system to be reacted was controlled to be stirred for about 18 minutes at 400 rpm at 155° C. to 160° C., a large amount of solids were generated, then a stirring speed was reduced to 200 rpm, the temperature was controlled between 155° C. to 160° C. by cooperation of microwave heating and condensation of external condensation equipment, and this temperature was totally controlled for 60 minutes, so as to obtain a product system. Then the temperature of the product system was cooled to 90° C., 3 v (360 mL) ethanol was added into it for stirring and washing, filtering was carried out to obtain a filter cake, this filter cake was stirred and washed with 2 v (240 mL) ethanol, filtered and dried, and through nuclear magnetism verification, an obtained product was metformin hydrochloride. The power of the above microwave heating was 500 W, and the reaction kettle was set to be open in the reaction process, so as to control the pressure in the reaction process to be about the normal pressure.

Embodiment 6

Dicyandiamide (120 g), dimethylamine hydrochloride (139.7 g), and diphenyl (120 mL) at a molar ratio of 1:1:1 were added into a glass reaction kettle to be mixed to form a mixed system. The mixed system was dissolved under the conditions of microwave heating and stirring at 400 rpm to form a system to be reacted. Microwave heating was utilized to increase the temperature of the system to be reacted to 155° C. 5 mg of metformin hydrochloride was added as a crystal nucleus at 155° C. After the system to be reacted was controlled to be stirred for about 18 minutes at 400 rpm at 155° C. to 160° C., a large amount of solids were generated, then a stirring speed was reduced to 200 rpm, the temperature was controlled between 155° C. to 160° C. by cooperation of microwave heating and condensation of external condensation equipment, and this temperature was totally controlled for 60 minutes, so as to obtain a product system. Then the temperature of the product system was cooled to 90° C., 3 v (360 mL) ethanol was added into it for stirring and washing, filtering is carried out to obtain a filter cake, this filter cake was stirred and washed with 2 v (240 mL) ethanol, filtered and dried, and through nuclear magnetism verification, an obtained product is metformin hydrochloride. The power of the above microwave heating was 500 W, and the reaction kettle was set to be open in the reaction process, so as to control the pressure in the reaction process to be about the normal pressure.

Embodiment 7

Dicyandiamide (120 g), dimethylamine hydrochloride (139.7 g), and N-methylpyrrolidone (360 mL) at a molar ratio of 1:1:3 were added into a glass reaction kettle to be mixed to form a mixed system. The mixed system was dissolved under the conditions of microwave heating and stirring at 400 rpm to form a system to be reacted. Microwave heating was utilized to increase the temperature of the system to be reacted to 155° C. 5 mg of metformin hydrochloride was added as a crystal nucleus at 155° C. After the system to be reacted was controlled to be stirred for about 18 minutes at 400 rpm at 155° C. to 160° C., a large amount of solids were generated, then a stirring speed was reduced to 200 rpm, the temperature was controlled between 155° C. to 160° C. by cooperation of microwave heating and condensation of external condensation equipment, and this temperature was totally controlled for 60 minutes, so as to obtain a product system. Then the temperature of the product system was cooled to 90° C., 3 v (360 mL) ethanol was added into it for stirring and washing, filtering was carried out to obtain a filter cake, this filter cake was stirred and washed with 2 v (240 mL) ethanol, filtered and dried, and through nuclear magnetism verification, an obtained product was metformin hydrochloride. The power of the above microwave heating was 500 W, and the reaction kettle was set to be open in the reaction process, so as to control the pressure in the reaction process to be about the normal pressure.

Embodiment 8

Dicyandiamide (120 g), dimethylamine hydrochloride (139.7 g), and cyclohexanol (360 mL) at a molar ratio of 1:1.2:3 were added into a glass reaction kettle to be mixed to form a mixed system. The mixed system was dissolved under the conditions of microwave heating and stirring at 400 rpm to form a system to be reacted. Microwave heating was utilized to increase the temperature of the system to be reacted to 155° C. After the system to be reacted was controlled to be stirred for about 25 minutes at 400 rpm at 155° C. to 160° C., a large amount of solids were generated, then a stirring speed was reduced to 200 rpm, the temperature was controlled between 155° C. to 160° C. by cooperation of microwave heating and condensation of external condensation equipment, and this temperature was totally controlled for 80 minutes, so as to obtain a product system. Then the temperature of the product system was cooled to 90° C., 3 v (360 mL) ethanol was added into it for stirring and washing, filtering was carried out to obtain a filter cake, this filter cake was stirred and washed with 2 v (240 mL) ethanol, filtered and dried, and through nuclear magnetism verification, an obtained product was metformin hydrochloride. The power of the above microwave heating was 500 W, and the reaction kettle was set to be open in the reaction process, so as to control the pressure in the reaction process to be about the normal pressure.

Embodiment 9

Dicyandiamide (120 g), dimethylamine hydrochloride (139.7 g), and cyclohexanol (360 mL) at a molar ratio of 1:1.2:3 were added into a glass reaction kettle to be mixed to form a mixed system. The mixed system was dissolved under the conditions of microwave heating and stirring at 400 rpm to form a system to be reacted. Microwave heating was utilized to increase the temperature of the system to be reacted to 150° C. 5 mg of metformin hydrochloride was added as a crystal nucleus at 150° C. After the system to be reacted was controlled to be stirred for about 18 minutes at 400 rpm at 155° C. to 160° C., a large amount of solids were generated, then a stirring speed was reduced to 250 rpm, the temperature was controlled between 155° C. to 160° C. by cooperation of microwave heating and condensation of external condensation equipment, and this temperature was totally controlled for 60 minutes, so as to obtain a product system. Then the temperature of the product system was cooled to 90° C., 3 v (360 mL) ethanol was added into it for stirring and washing, filtering was carried out to obtain a filter cake, this filter cake was stirred and washed with 2 v (240 mL) ethanol, filtered and dried, and through nuclear magnetism verification, an obtained product was metformin hydrochloride. The power of the above microwave heating was 500 W, and the reaction kettle was set to be open in the reaction process, so as to control the pressure in the reaction process to be about the normal pressure.

Embodiment 10

Dicyandiamide (120 g), dimethylamine hydrochloride (139.7 g), and cyclohexanol (360 mL) at a molar ratio of 1:1:3 were added into a glass reaction kettle to be mixed to form a mixed system. The mixed system was dissolved under the conditions of microwave heating and stirring at 300 rpm to form a system to be reacted. Microwave heating was utilized to increase the temperature of the system to be reacted to 155° C. 5 mg of metformin hydrochloride was added as a crystal nucleus at 155° C. After the system to be reacted was controlled to be stirred for about 20 minutes at 300 rpm at 155° C. to 160° C., a large amount of solids were generated, then a stirring speed was reduced to 100 rpm, the temperature was controlled between 155° C. to 160° C. by cooperation of microwave heating and condensation of external condensation equipment, and this temperature was totally controlled for 90 minutes, so as to obtain a product system. Then the temperature of the product system was cooled to 90° C., 3 v (360 mL) ethanol was added into it for stirring and washing, filtering was carried out to obtain a filter cake, this filter cake was stirred and washed with 2 v (240 mL) ethanol, filtered and dried, and through nuclear magnetism verification, an obtained product was metformin hydrochloride. The power of the above microwave heating was 500 W, and the reaction kettle was set to be open in the reaction process, so as to control the pressure in the reaction process to be about the normal pressure.

Embodiment 11

Dicyandiamide (120 g), dimethylamine hydrochloride (139.7 g), and cyclohexanol (360 mL) at a molar ratio of 1:1:3 were added into a ceramic reaction kettle to be mixed to form a mixed system. The mixed system was dissolved under the conditions of microwave heating and stirring at 400 rpm to form a system to be reacted. Microwave heating was utilized to increase the temperature of the system to be reacted to 155° C. 5 mg of metformin hydrochloride was added as a crystal nucleus at 155° C. After the system to be reacted is controlled to be stirred for about 18 minutes at 300 rpm at 155° C. to 160° C., a large amount of solids were generated, then a stirring speed was reduced to 300 rpm, the temperature was controlled between 155° C. to 160° C. by cooperation of microwave heating and condensation of external condensation equipment, and this temperature was totally controlled for 50 minutes, so as to obtain a product system. Then the temperature of the product system was cooled to 90° C., 3 v (360 mL) ethanol was added into it for stirring and washing, filtering was carried out to obtain a filter cake, this filter cake was stirred and washed with 2 v (240 mL) ethanol, filtered and dried, and through nuclear magnetism verification, an obtained product was metformin hydrochloride. The power of the above microwave heating was 500 W, and the reaction kettle was set to be open in the reaction process, so as to control the pressure in the reaction process to be about the normal pressure.

Embodiment 12

Dicyandiamide (120 g), dimethylamine hydrochloride (139.7 g), and cyclohexanol (360 mL) at a molar ratio of 1:1:3 were added into a ceramic reaction kettle to be mixed to form a mixed system. The mixed system was dissolved under the conditions of microwave heating and stirring at 500 rpm to form a system to be reacted. Microwave heating was utilized to increase the temperature of the system to be reacted to 155° C. 5 mg of metformin hydrochloride was added as a crystal nucleus at 155° C. After the system to be reacted was controlled to be stirred for about 18 minutes at 300 rpm at 155° C. to 160° C., a large amount of solids were generated, then a stirring speed was reduced to 150 rpm, the temperature was controlled between 155° C. to 160° C. by cooperation of microwave heating and condensation of external condensation equipment, and this temperature was totally controlled for 80 minutes, so as to obtain a product system. Then the temperature of the product system was cooled to 90° C., 3 v (360 mL) ethanol was added into it for stirring and washing, filtering was carried out to obtain a filter cake, this filter cake was stirred and washed with 2 v (240 mL) ethanol, filtered and dried, and through nuclear magnetism verification, an obtained product was metformin hydrochloride. The power of the above microwave heating was 500 W, and the reaction kettle was set to be open in the reaction process, so as to control the pressure in the reaction process to be about the normal pressure.

Embodiment 13

The differences from Embodiment 1 lied in that the power of the above microwave heating was 100 W, and that a large amount of solids were generated after the system to be reacted is stirred for about 30 minutes.

Embodiment 14

The differences from Embodiment 1 lied in that the power of the above microwave heating was 1000 W, and that a large amount of solids were generated after the system to be reacted was stirred for about 10 minutes.

Embodiment 15

Dicyandiamide (120 g), dimethylamine hydrochloride (139.7 g), and cyclohexanol (360 mL) at a molar ratio of 1:1:3 were added into a glass reaction kettle to be mixed to form a mixed system. The mixed system was dissolved under the conditions of microwave heating and stirring at 400 rpm to form a system to be reacted. Microwave heating was utilized to increase the temperature of the system to be reacted to 100° C. 5 mg of metformin hydrochloride was added as a crystal nucleus at 100° C. After the system to be reacted was controlled to be stirred for about 12 hours at 400 rpm at 100° C. to 110° C., a large amount of solids were generated, then a stirring speed was reduced to 200 rpm, the temperature was controlled between 100° C. to 110° C. by cooperation of microwave heating and condensation of external condensation equipment, and this temperature was totally controlled for 12 hours, so as to obtain a product system. Then the temperature of the product system was cooled to 90° C., 3 v (360 mL) ethanol was added into it for stirring and washing, filtering was carried out to obtain a filter cake, this filter cake was stirred and washed with 2 v (240 mL) ethanol, filtered and dried, and through nuclear magnetism verification, an obtained product was metformin hydrochloride. The power of the above microwave heating was 500 W, and the reaction kettle was set to be open in the reaction process, so as to control the pressure in the reaction process to be about the normal pressure.

The purity and yields of the products obtained in the above embodiments are tested and calculated, and obtained results are shown in Table 1.

TABLE 1

| Embodiments | System purity (HPLC) (%) | Yield (%) | Purity after first purification (%) |
| --- | --- | --- | --- |
| 1 | 93.8 | 86.3 | 99.98 |
| 2 | 91.69 | 87 | 99.98 |
| 3 | 68.5 | 61 | 99.98 |
| 4 | 66.7 | 60 | 99.82 |
| 5 | 92.7 | 89 | 99.89 |
| 6 | 92.3 | 87.6 | 99.76 |
| 7 | 92.1 | 87.2 | 99.93 |
| 8 | 92.42 | 87.42 | 99.96 |
| 9 | 92.96 | 89.73 | 99.96 |
| 10 | 90.24 | 84.75 | 99.92 |
| 11 | 94.06 | 86.9 | 99.99 |
| 12 | 94.1 | 85.61 | 99.99 |
| 13 | 92.3 | 85.2 | 99.98 |
| 14 | 93.9 | 86.3 | 99.98 |
| 15 | 85.24 | 82.4 | 99.98 |

According to the comparison of the above embodiments, it can be seen that the selection of the solvent has a certain impact on the yield and purity of the metformin hydrochloride; the addition of the crystal nucleus has no substantial impact on the purity and reaction yield, and its main action is to shorten the reaction time; moreover, if the pressure is too high during the reaction, the yield of the metformin hydrochloride will be reduced; in addition, changes in the stirring speed will affect the reaction time, yield and purity.

From the above descriptions, it can be seen that the above embodiments of the present invention achieve the following technical effects:

The present application adopts a microwave technology for heating. The microwave technology has strong penetration and can make the material system reach the state of heating inside and outside almost at the same time to form a state of body heat source, greatly shortening the heat transfer time in conventional heating, and making the inside and outside of the materials uniformly heated, generating less by-products and making high conversion rate. Molecules and ions in the material system undergo repeated and rapid orientation and rotation under the action of a microwave high-frequency electric field, or absorb microwave energy to increase thermal motion energy, which can also improve the reaction efficiency of the molecules. The thermal inertia of microwave heating is small, and the microwave heats the system instantaneously, which is low in energy consumption, and economical and environmentally friendly. On the other hand, the power of the microwave can be adjusted at any time, and there is no "waste heat" phenomenon, which is extremely conducive to the needs of automatic control and continuous production.

In addition, the preparation method of the present application is suitable for the melting method or the solvent method, especially the use of the melting method or the use of the cyclohexanol as the solvent greatly reduces the biological toxicity that may be introduced, and reduces the difficulty of its subsequent processing. This technology can realize the reaction under the normal pressure (standard atmospheric pressure). Meanwhile, the use of the microwave technology and condensation technology greatly improves its process safety.

The above-mentioned descriptions are only preferred embodiments of the present disclosure and are not used to limit the present disclosure. For those skilled in the art, the present disclosure can have various modifications and changes. Any modification, equivalent replacement, improvement, etc., made within the spirit and principle of the present disclosure should be included in the scope of protection of the present disclosure.

What is claimed is:

1. A preparation method for metformin hydrochloride, wherein the preparation method comprises:
   microwave heating raw materials containing dicyandiamide and dimethylamine hydrochloride, and reacting the two at 100° C. to 160° C. to obtain a product system containing metformin hydrochloride; and
   wherein in the preparation method, metformin hydrochloride crystal nuclei are added when the temperature of the system is reacted from 100° C. to 160° C., and wherein the weight ratio of the metformin hydrochloride crystal nuclei to the dicyandiamide is 0.0015-0.0045:100.

2. The preparation method according to claim 1, wherein the preparation method comprises:
   mixing the dicyandiamide and the dimethylamine hydrochloride to form a first mixed system;
   microwave heating and melting the first mixed system to obtain a system that is reacted; and
   controlling the temperature of the system that is reacted at 100° C. to 160° C. for reaction, so as to obtain the product system.

3. The preparation method according to claim 1, wherein the preparation method comprises:
   mixing a solvent, the dicyandiamide and the dimethylamine hydrochloride to form a second mixed system;
   microwave heating the second mixed system to dissolve the dicyandiamide and the dimethylamine hydrochloride into the solvent to form a system that is reacted; and
   controlling the temperature of the system that is reacted at 100° C. to 160° C., so as to obtain the product system.

4. The preparation method according to claim 3, wherein the solvent is selected from the group consisting of ethanol, cyclohexanol, mesitylene, diphenyl and N-methylpyrrolidone, and the molar ratio of the dicyandiamide to the solvent is 1:1 to 1:5.

5. The preparation method according to claim 2, wherein the molar ratio of the dicyandiamide to the dimethylamine hydrochloride is 1:1 to 1:2.

6. The preparation method according to claim 2, wherein the temperature of the system that is reacted is controlled between 100° C. to 160° C. by cooperation of intermittent microwave heating and external condensation.

7. The preparation method according to claim 2, wherein the process of forming the system that is reacted and the reaction process of the system that is reacted are carried out under stirring, the stirring speed in the process of forming the system that is reacted is 300 rpm to 400 rpm, the stirring speed in the reaction process of the system that is reacted is 100 rpm to 400 rpm, and the system that is reacted precipitates crystals as the reaction processes, and the stirring speed in a crystallization phase in the reaction process of the system that is reacted is 100 rpm to 300 rpm.

8. The preparation method according to claim 1, wherein the power of the microwave heating is 100 W to 1000 W.

9. The preparation method as according to claim 2, wherein the reaction pressure in the reaction process of the system that is reacted is controlled between 95 KPa to 105 KPa.

10. The preparation method according to claim 2, wherein the temperature after crystals are precipitated in the system that is reacted is kept for 30 minutes to 60 minutes.

11. The preparation method according to claim 1, wherein the preparation method further comprises a process of purifying the metformin hydrochloride from the product system, the process of purifying the metformin hydrochloride comprises:
   cooling the temperature of the product system to 85° C. to 95° C., and then mixing the product system with ethanol to form a solid-liquid mixed system;
   subjecting the solid-liquid mixed system to solid-liquid separation to obtain a solid product and a liquid isolate; and
   washing the solid product with ethanol, carrying out solid-liquid separation and drying, so as to obtain purified metformin hydrochloride.

12. The preparation method according to claim 3, wherein the molar ratio of the dicyandiamide to the dimethylamine hydrochloride is 1:1 to 1:2.

13. The preparation method according to claim 3, wherein the temperature of the system that is reacted is controlled between 100° C. to 160° C. by cooperation of intermittent microwave heating and external condensation.

14. The preparation method according to claim 3, wherein the process of forming the system that is reacted and the reaction process of the system that is reacted are carried out under stirring, the stirring speed in the process of forming the system that is reacted is 300 rpm to 400 rpm, and the stirring speed in the reaction process of the system that is reacted is 100 rpm to 400 rpm, and the system that is reacted precipitates crystals as the reaction processes, and the stirring speed in a crystallization phase in the reaction process of the system that is reacted is more 100 rpm to 300 rpm.

15. The preparation method according to claim 2, wherein the power of the microwave heating is 100 W to 1000 W.

16. The preparation method according to claim 3, wherein the power of the microwave heating is 100 W to 1000 W.

17. The preparation method according to claim 3, wherein the reaction pressure in the reaction process of the system that is reacted is controlled between 95 KPa to 105 KPa.

18. The preparation method according to claim 3, wherein the system that is reacted precipitates crystals as the reaction processes, and the temperature after crystals are precipitated in the above system that is reacted is kept for 30 minutes to 60 minutes.

19. The preparation method according to claim 2, wherein the preparation method further comprises a process of purifying the metformin hydrochloride from the product system, the process of purifying the metformin hydrochloride comprises:
- cooling the temperature of the product system to 85° C. to 95° C., and then mixing the product system with ethanol to form a solid-liquid mixed system;
- subjecting the solid-liquid mixed system to solid-liquid separation to obtain a solid product and a liquid isolate; and
- washing the solid product with ethanol, carrying out solid-liquid separation and drying, so as to obtain purified metformin hydrochloride.

\* \* \* \* \*